United States Patent [19]

Jarrett et al.

[11] Patent Number: 5,512,279
[45] Date of Patent: Apr. 30, 1996

[54] BIOLOGICAL CONTROL OF DIPTERAN PESTS OF THE GENUS LYCORIELLA USING *BACILLUS THURINGIENSIS*

[75] Inventors: Paul Jarrett; Philip F. White; Nicole J. Pethybridge, all of West Sussex, England

[73] Assignee: Agricultural Genetics Company Limited, Cambridge, England

[21] Appl. No.: 39,201

[22] PCT Filed: Nov. 7, 1991

[86] PCT No.: PCT/GB91/01957

§ 371 Date: Apr. 15, 1993

§ 102(e) Date: Apr. 15, 1993

[87] PCT Pub. No.: WO92/08354

PCT Pub. Date: May 29, 1992

[30] Foreign Application Priority Data

Nov. 8, 1990 [GB] United Kingdom ............. 9024296
Apr. 9, 1991 [GB] United Kingdom ............. 9107397

[51] Int. Cl.$^6$ ..................... A01N 63/00; C12N 1/20
[52] U.S. Cl. ..................... 424/93.461; 435/252.5; 435/832
[58] Field of Search ............. 424/93 L, 93.461; 435/252.5, 832

[56] References Cited

U.S. PATENT DOCUMENTS

| | | | |
|---|---|---|---|
| 4,061,488 | 12/1977 | Mann | 71/77 |
| 4,695,462 | 9/1987 | Barnes et al. | 424/195.1 |
| 4,975,105 | 12/1990 | Kremer et al. | 71/6 |
| 5,106,620 | 4/1992 | Nickle et al. | 424/93 L |
| 5,106,648 | 4/1992 | Williams | 427/3 |
| 5,185,148 | 2/1993 | Michaels | 424/93 L |
| 5,208,017 | 5/1993 | Bradfisch et al. | 424/93 L |
| 5,211,946 | 5/1993 | Payne et al. | 424/93 L |
| 5,262,160 | 11/1993 | Payne | 424/94.1 |
| 5,262,323 | 11/1993 | Baird et al. | 435/252.5 |
| 5,266,483 | 11/1993 | Iizuka et al. | 435/252.5 |
| 5,275,815 | 1/1994 | Payne | 424/93 L |
| 5,277,906 | 1/1994 | Zaehner et al. | 424/93 L |
| 5,298,245 | 3/1994 | Payne et al. | 424/93 K |

OTHER PUBLICATIONS

Rodcharoen, J., et al., "J. Amer. Mosquito Control Assoc.," vol. 7, pp. 56–62, 1991.
Keil, C. B., "Mushroom News," vol. 36, pp. 4–10, 1988.
Alten, B., et al., "Doga—Tr. J. of Zoology," vol. 14, pp. 263–273, 1990.
Branco, Jr., A. C., et al., "Mem. Inst. Oswaldo Cruz," vol. 87, pp. 317–318, 1992.
White, P. F., et al., "Brighten Crop Protection Conference, Pests & Diseases," 1990, pp. 373–378. vol. 1.
Cantwell, G. E., et al., "J. of Econ. Entomol.," vol. 77, pp. 473–475, 1984.
Keil, C. B., "J. of Econ. Entomol.," vol. 84(4), pp. 1180–1188, 1991.
Osborne, L. S., et al., "J. of Econ. Entomol.," vol. 78, pp. 922–925, 1985.
De Moor, F. C., et al., "Onderstepoort J. Vet. Res.," vol. 53(1), pp. 43–50, 1986.
"Coprecipitation with Lactose as a Means of Recovering the Spore–Crystal Complex of *Bacillus thuringiensis*", H. T. Dulmage et al., Journal of Invertebrate Pathology, pp. 15–20, (1970) vol. 15.
"Laboratory Rearing, Biology and Chemical Control of the Mushroom Sciarid *Lycoriella auripila*", E. S. Binns, Annals of Applied Biology, pp. 119–126, (1973) vol. 73.

*Primary Examiner*—Michael G. Wityshyn
*Assistant Examiner*—Kristin Larson
*Attorney, Agent, or Firm*—Lowe, Price, LeBlanc & Becker

[57] ABSTRACT

The invention relates to the biological control of Dipteran pests other than the mosquito, which comprises the use of *Bacillus thuringiensis* isolate HD 541 (NCIMB 40373) or HD 571 (NCIMB 40374), or a mutant, recombinant or derivative thereof, or insecticidal material derived therefrom.

4 Claims, No Drawings

BIOLOGICAL CONTROL OF DIPTERAN PESTS OF THE GENUS LYCORIELLA USING *BACILLUS THURINGIENSIS*

This invention relates to biological methods of pest control and more particularly to methods and compositions utilizing *Bacillus thuringiensis* for the control of agricultural, horticultural and public health pests.

*Bacillus thuringiensis* is a spore forming bacterium which has long been known to kill insects. Many hundreds of isolates (strains) of this species have been listed. Cultures of these isolates are catalogued and maintained by the Agricultural Research Services of the US Department of Agriculture, Peoria, Ill., and a number of other international collections, and are available to researchers on request. The release of some cultures require the permission of the contributor to the culture collection but most are available without any conditions. The spectrum of activity of these isolates and their potency against particular insects vary very widely.

The present invention comprises the use of *B. thuringiensis* isolates HD541 and HD571 for the control of Dipteran pests which affect plants and edible fungi. Accordingly the invention comprises a method of pest control in which agricultural and horticultural produce are protected against pests by the application of isolates of the sub-species *kyushuensis* to the growing plants or other horticultural products or to their growing locations. The invention also comprises compositions containing one or more *B. thuringiensis* isolates formulated for agricultural, horticultural or public health application. The two isolates, listed as HD 541 and HD 571 in the US culture collection mentioned above, have shown excellent promise for the purposes of the present invention. These have been available at the US culture collection since August 1979 (HD541) and December 1979 (HD571) and are available without restriction. However, in order to ensure their continued availability we have deposited them on Mar. 8th 1991 with the National Collection of Industrial and Marine Bacteria, 23 St. Machar Drive, Aberdeen AB2 IRY, Scotland under the Budapest Treaty. The deposited strains have been given Accession numbers NCIMB 40373 (HD541) and NCIMB 40374 (HD571).

The *B. thuringiensis* isolates HD541 and HD571 are known to have an effect on the dipteran insect *Aedes aegypti* (mosquito). However the level of activity against this insect is low, being approximately ten thousand-fold less than that of *B. thuringiensis israelensis*, the sub-species which is currently used for mosquito control. Isolates HD541 and HD571 have also been tested against other mosquito species but their potency was found to be too low to be useful for practical purposes.

It has now been found that the named isolates are highly potent insecticides for certain Dipteran pests other than the mosquito, especially for plant and mushroom pests such as the sciarid fungus gnats. The isolates of the invention, i.e. HD541 and HD571 are highly active against larvae of the mushroom sciarid *Lycoriella auripila*, the most damaging pest of mushroom crops in the UK, which causes severe losses in crop yield and is at present controlled mainly by the chemical insecticide diflubenzuron. A similar species, *L. mali*, occupies the same niche in the USA and Australia. The activity of the named isolates against these pests is significantly greater than that of other isolates of *B. thuringiensis* including some from each of the sub-species *israelensis, dendrolimus, kyushuensis* and *morrisoni*. The named isolates thus provide much needed new agents for the control of these pests. In addition to the sciarids, other mushroom pests which may be controlled by these isolates are the mushroom phorids. However, the named isolates do not have unusually good activity against mushroom cecid pests. Other Dipteran pests of agricultural significance include the Mediterranean fruit fly.

As indicated, the present invention utilises the natural isolates HD541 and HD571. The invention is applicable also to mutants, recombinants and derivatives of the natural isolates and which are active against Dipteran pests. Such derivatives include those obtained by genetic manipulation. The invention also includes the use of delta endotoxins derived from the above-mentioned organisms.

The invention provides an entomocidal substance derived from *Bacillus thuringiensis* strain HD541 or HD571, or from a derivative or mutant thereof. In one embodiment the entomocidal substance is a spore-crystal complex.

The invention further provides an entomocidal substance derived from *Bacillus thuringiensis* strain HD541 (NCIMB 40373) or HD571 (NCIMB 40374) or a derivative or mutant thereof, or an entomocidal substance as defined above together with an agricultural adjuvant such as a carrier, diluent, surfactant or application-promoting adjuvant. The composition may also contain a further biologically active compound selected from fertilizers, micronutrient donors, plant growth preparations, herbicides, insecticides, fungicides, bactericides, nematicides and molluscicides and mixtures thereof. The composition may comprise from 0.1 to 99% by weight of *Bacillus thuringiensis* HD541 or HD571 or the derivative or mutant thereof, or the entomocidal substance; from 1 to 99.9% by weight of a solid or liquid adjuvant and from 0 to 25% by weight of a surfactant.

The invention in addition provides a method of combatting pests which comprises applying to the pests or to their environment an entomocidally effective amount of *Bacillus thuringiensis* strain HD541 or HD571, or a derivative or mutant thereof, or an entomocidal substance as defined above, or a composition containing said strain, derivative, mutant or substance.

The strains of *Bacillus thuringiensis* HD541 or HD571 or the compositions containing them may be administered to the plants or crops to be protected together with other insecticides or chemicals without loss of potency.

It is compatible with most other commonly used agricultural spray materials but should not be used in extremely alkaline spray solutions.

It may be administered as a dust, a suspension, a wettable powder or in any other material form suitable for agricultural application.

During production by fermentation, after normal growth of *Bacillus thuringiensis*, the mother cells lyse and release the spores and crystals into the growth medium. The spores and crystals may be harvested by centrifugation or filtration, spray drying, vacuum drying, or a method of precipitation, such as the lactose coprecipitation technique as reported by Dulmage et al (Journal of Invertebrate Pathology, 15, 15–20, 1970). The resulting spore-crystal complex is stable for long periods and can be formulated into a product suitable for application to crops.

A method for preparing an insecticidal composition according to the invention, comprises culturing the *Bacillus thuringiensis* strain HD541 or HD571 by:

a) maintaining the strain in lyophilized ampules,
b) inoculating with the strain on agar slopes,
c) incubating these slopes for 1 to 5 days at 20° to 40° C., preferably 25° to 33° C.
d) inoculating from these slopes into shaken flasks containing an aqueous culture medium, e) shaking this container at a temperature of 20° to 40° C. preferably 30° C. for 1 to 5, preferably 1 to 2 days and optionally repeating this vegetative growth stage at least once in a separate flask, f) inoculating in a preculture fermenter an aqueous cultivating medium with the cultures of stage e), g) stirring and aerating the medium containing the inoculate at a temperature of 20° to 40° C., preferably 30° to 35° C., and optionally repeating this preculture fermentation stage at least once in a separate larger container, h) introducing 2 to 20 per cent by weight of the incubating liquor of stage g) into a production fermenter, containing an aqueous cultivating medium, i) stirring and aerating the medium at a temperature of 20° to 40° C., preferably 30° to 35° C.

j) harvesting the *Bacillus thuringiensis* HD541 or HD571 broth when sporulation and crystal production in the production fermenter reaches a maximum.

k) the agar and broth in a to d should contain at least one nitrogen source, at least one carbon source and at least one salt, preferably peptone, glucose and at least one salt. The media in f to j should contain at least one nitrogen source (eg peptone, yeast extract, corn steep liquor, soya bean meal, cotton seed meal, fishmeal), at least one carbohydrate source (eg glucose, lactose, sucrose, starch or raw material rich in these constituents) and at least one mineral salt. The nitrogen and carbohydrate should be balanced to exhaust as near as possible simultaneously.

The spore-crystal complex or the composition containing it may be administered to the plants or crops to be protected together with certain other insecticides or chemicals without loss or potency.

It is possible to kill the spores in the spore-crystal (eg by gamma irradiation), or to avoid producing spores by use of an asporogenous crystaliferous mutant, thereby producing a non-viable product. A non-viable product may be advantageous in certain circumstances where it is desired to prevent the spread of bacteria for aesthetic reasons or to avoid causing disease in beneficial insects. However, non-viable products are generally not as active as those containing live spores and as a further disadvantage there is the increased cost of killing the spores.

The invention furthermore relates to a method of treating crops which comprises applying an entomocidally effective amount of *B. thuringiensis* HD541 or HD571, or a composition thereof.

*Bacillus thuringiensis* HD541 or HD571, is normally applied in the form of compositions and can be applied to the crop area to be treated, simultaneously or in succession, with further biologically active compounds. These compounds may be both fertilizers or micronutrient donors or other preparations that influence plant growth. They may also be selective herbicides, insecticides, fungicides, bactericides, nematicides, molluscicides or mixtures of several of these preparations, if desired together with further carriers, surfactants or application-promoting adjuvants customarily employed in the art of formulation. Suitable carriers and adjuvants can be solid or liquid and correspond to the substances ordinarily employed in formulation technology, eg natural or regenerated mineral substances, solvents, dispersants, wetting agents, tackifiers, binders or fertilizers.

The formulations, ie the compositions, preparations or mixtures containing *B. thuringiensis* HD541 or HD571 as an active ingredient or combinations thereof with other active ingredients, and, where appropriate, a solid or liquid adjuvant, are prepared in known manner eg by homogeneously mixing and/or grinding the active ingredients with extenders eg solvents, solid carriers and in some cases surface-acting compounds (surfactants).

Suitable solvents are: aromatic hydrocarbons, preferably the fractions containing 8 to 12 carbon atoms, eg xylene mixtures or substituted napthalenes, phthalates such as dibutylphthalate or dioctylphthalate, aliphatic hydrocarbons such as cyclohexane or paraffins, alcohols and glycols, such as cyclohexanone, strongly polar solvents such as N-methyl-2-pyrrolidone, dimethylsulfoxide or dimethylformamide as well as vegetable oils or epoxidized vegetable oils such as epoxidized coconut oil or soybean oil; or water.

The solid carriers used eg for dusts and dispersable powders, are normally natural mineral fillers such as calcite, talcum, kaolin, montmorillonite or attapulgite. In order to improve the physical properties of the carriers it is possible to add highly dispersed silicic acid or highly dispersed absorbent polymers. Suitable granulated adsorptive carriers are porous types, for example pumice, broken brick, sepiolite or bentonire; and suitable nonsorbent carriers are materials such as calcite or sand. In addition, a great number of pregranulated materials of inorganic or organic nature can be used, eg especially dolomite or pulverised plant residues.

Depending on the nature of the active ingredients to be formulated, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$-$C_{22}$), eg the sodium or potassium salts of oleic or stearic acid, or of natural fatty acid mixtures which can be obtained, eg from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylaryl-sulfonates.

The fatty sulfonates or sulfates are usually in the forms of alkali metal salts, alkaline earth metal salts or unsubstituted or substituted ammonium salts and generally contain a $C_8$-$C_{22}$ alkyl radical which also includes the alkyl moiety of acyl radicals, eg the sodium or calcium salt of lignosulfonic acid, or dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing about 8 to 22 carbon atoms. Examples of alkyl-arylsufonates are the sodium, calcium or triethanolamine salts of dodecylbenzenesulfonic acid, dibutylnapththalenesulfonic acid or of a naphthalenesulfonic acid/formaldehyde condensation product. Also suitable are corresponding phosphates, eg salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypol yethoxyethanol, polyethylene glycol and octylphenoxypol yethoxyethanol. Fatty acid esters of polyoxyethylene sorbitan, such as polyoxyethylene sorbitan trioleate, are also suitable non-ionic surfactants.

Cationic surfactants are preferably quaternary ammonium salts which contain, as N-substituent, at least one $C_8$-$C_{22}$ alkyl radical and, as further substituents, lower unsubstituted or halogenated alkyl, benzyl or hydroxyl-lower alkyl radicals. The salts are preferably in the form of halides, methylsulfates or ethyl sulfates eg stearyltrimethylammonium chloride or benzyldi-( 2-chloroethyl ) ethylammonium bromide.

The surfactants customarily employed in the art of formulation are described eg in "McCutcheon's Detergents and Emulsifiers Annual", MC Publishing Corp, Ridgewood, N.J., 1979; Dr Helmut Stache, "Tensid Taschenbuch" (Handbook of Surfactants ), Carl Hanser Verlag, Munich/Vienna.

The entomocidal compositions usually contain 0.1 to 99%, preferably 0.1 to 95% of Bacillus thuringiensis HD541 or HD571, or combination thereof with other active ingredients, 1 to 99.9% of a solid or liquid adjuvant and 0 to 25%, preferably 0.1 to 20%, of a surfactant.

Whereas commercial products are preferably formulated as concentrates, the end user will normally employ dilute formulations of substantially lower concentration.

The compositions may also contain further ingredients, such as stabilizers, antifoams, viscosity regulators, binders, tackifiers as well as fertilizers or other active ingredients in order to obtain special effects.

The invention will now be further described with reference to experimental and field test data obtained in comparative testing of isolates HD541 and HD571 and of other B. thuringiensis isolates.

EXAMPLE 1—Bacterial Culture

Bacteria were grown at 30° C. in 50 ml of a growth medium, contained in 250 ml fluted flask on an orbital shaker at 250 rpm and inoculated at a rate of 1% v/v with a mid-exponential phase culture. A typical growth medium comprised 10 g/l soymeal, 10 g/l potato starch, 5 g/l $K_2HPO_4$ and 10 ml/l trace elements solution. The trace elements solution comprised 8 g/l $CaCl_2$. $2H_2O$, 5 g/l $MnCl_2$. $2H_2O$ and 0.5 g/l of each of $CuCl_2$. $2H_2O$, $ZnCl_2$, $CoCl_2$ and $FeCl_3$. Cultures were monitored by phase-contrast microscopy and harvested upon complete autolysis of the cells. Duration of incubation ranged from 40 to 72h, depending on the isolate. Preparation of the growth medium and conversion of cultures into dry powders by the lactose-acetone method were as described by Dulmage et al (Journal of Invertebrate Pathology 1970, 15, 15– 20). Production of bacteria for mushroom trials was the same as above except that 400ml of broth was used in 2 l fluted flasks and the broth was not made into a powder.

EXAMPLE 2—Insect Bioassays

For the laboratory bioassay, bacterial powders were homogenized in de-ionized water, diluted as appropriate and 10 ml volumes mixed into 40 g of a peat: soya-flour mixture (20:1). The treated medium was then equally split into two plastic pots (A. W. Gregory Ltd, London) and a minimum of 20 neonate Lycoriella auripila or L. mali larvae added per pot. Eggs and larvae of L. auripila or L. mali were obtained using the method devised by Binns (Annals of Applied Biology 1973, 73, 119–126). Pots were incubated at 24° C. and subsequent emergence of adults recorded daily. Emergence of adults from eight control pots without B. thuringiensis was used for treatment comparisons.

All isolates were initially tested at the rate of 10 mg of bacterial powder per g of medium. Those strains which caused greater than 95% mortality were re-tested in greater detail using a range of concentrations. All data were analyzed by Probit analysis.

Activity of the B. thuringiensis isolates against L. auripila varied considerably, with 9 out of 22 isolates having good to moderate activity (Table 1). Strains belonging to sub-species morrisoni, darmstadiensis, kyushuensis, and israelensis were the most active. Flies emerging from treatments containing sublethal doses of B. thuringiensis also took longer to develop through to the fly stage than did the controls. Development times were, on average, 4 days longer in those treatments which caused greater than 50% mortality in laboratory assays. Statistical analysis of the bioassay data showed that isolates HD541 and HD571 were significantly more active than any of the others rested.

In separate tests, isolates HD541 and HD571 were found to be significantly more active against L. auripila than other isolates belonging to sub-species kyushuensis.

A comparison was made of the activity of gamma-irradiated samples of isolates HD571 and IPS82 against L. mali. B. thuringiensis isolate HD571 was found to be significantly more active ($LC_{50}$ 44.4 ug per g, fiducial limits 27.40–58.75) than B thuringiensis israelensis isolate IPS82, which had an $LC_{50}$ value in excess of 100 ug per g.

EXAMPLE 3—Mushroom Trials

Spawn-run mushroom compost, was put into 48, 25 cm plastic plant pots at a rate of 2.5 kg per pot. A moist casing mixture, consisting of equal volumes of peat and chalk, was added to the surface of the compost at a rate of 1.5 kg per pot. Previous to its application, the casing was either left untreated; treated with diflubenzuron at 30 mg a. i./kg —the standard commercial control chemical and rate; or treated with broth cultures or formulations of the strains at four rates: 0.4, 2, 10, or 50 ml/kg of casing for HD 541 and 4.0, 10.0, 25.0 or 62.5 ml/kg of casing for HD 571. The six treatments were each replicated eight times.

Six pots, one from each treatment, were arranged at random in a wooden mushroom tray (0.9×0.6m) and placed into a mushroom chamber. There were 8 trays in all, arranged into two stacks of 4. The chamber contained a high population of L. auripila adults. After 7 days the adults were killed with an aerial application of synthetic pyrethroids to prevent further egg laying. Eleven days after treatment, sticky traps were placed on top of the casing to catch emerging adults. The pots were then individually enclosed in fly-proof polyester netting. The traps were examined for flies 18, 22, 28 and 33 days after treatment. The air temperature within the chamber was maintained at 20° C. for the duration of the experiment.

Addition of broth cultures of the isolates HD541 and HD571 to the casing layer in the mushroom trials resulted in significant reduction in subsequent emergence of L. auripila adults compared to the untreated control (Table 2 (a)+(b)). HD 541 at 50 ml/kg and HD 571 at concentrations above 10 ml/kg gave comparable levels of control to that of the diflubenzuron treatment.

EXAMPLE 4

Formulation Examples for solid active ingredients of *Bacillus thuringiensis* HD541 or HD571 or combinations thereof with other active ingredients
(throughout, percentages are by weight)

1. Wettable powders

| | a) | b) | c) |
|---|---|---|---|
| *Bacillus thuringiensis* HD541 or HD571 | 25% | 50% | 75% |
| sodium lignosulfonate | 5% | 5% | — |
| sodium laurylsulfate | 3% | — | 5% |
| sodium diisobutylnapthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

*Bacillus thuringiensis* HD541 or HD571, is thoroughly mixed with the adjuvants and the mixture is thoroughly ground in a suitable mill, affording wettable powders which can be diluted with water to give suspensions of the desired concentration.

2. Emulsifiable concentrate

| | |
|---|---|
| *Bacillus thuringiensis* HD541 or HD571 | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

3. Dusts

| | a) | b) |
|---|---|---|
| *Bacillus thuringiensis* HD541 or HD571 | 5% | 8% |
| talcum | 95% | — |
| kaolin | — | 92% |

Ready for use dusts are obtained by mixing the active ingredient with the carriers and grinding the mixture in a suitable mill.

4. Extruder granulate

| | |
|---|---|
| *Bacillus thuringiensis* HD541 or HD571 | 10% |
| sodium lignosulfonate | 2% |
| carboxymethylcellulose | 1% |
| kaolin | 87% |

The active ingredient or combination is mixed and ground with the adjuvants and the mixture is subsequently moistened with water. The mixture is extruded, granulated and then dried in a stream of air.

5. Coated granulate

| | |
|---|---|
| *Bacillus thuringiensis* HD541 or HD571 | 3% |
| polyethylene glycol (mol. wt. 200 daltons) | 3% |
| kaolin | 94% |

The finely ground active ingredient or combination is uniformly applied in a mixter to the kaolin moistened with polyethylene glycol. Non-dusty coated granulates are obtained in this manner.

6. Suspension Concentrate

| | |
|---|---|
| *Bacillus thuringiensis* HD541 or HD571 | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient or combination is intimately mixed with the adjuvants giving a suspension concentrate from which suspensions of any desired concentration can be obtained by dilution with water.

EXAMPLE 5—Formulations: Efficacy Tests

A number of formulations of isolate HD571 were prepared as described in Example 4 and compared with unformulated culture broth and unformulated spray dried broth for control of *L. auripila* in a mushroom trial. The results, expressed as a percentage of pest control observed in diflubenzuron-treated pots, are summarized in Table 3. All preparations of isolate HD571 exhibit activity against *L. auripila* although the level of activity varies with the type of formulation. These represent examples of only a few effective formulations, preparation of many other effective formulations will be known to those skilled in the art.

TABLE 1

Activity of *Bacillus thuringiensis* against *Lycoriella auripila*.

| Code | Sub-species | $LC_{50}$ ug Et/g medium | Fiducial limits |
|---|---|---|---|
| IPS-82 | israelensis | 130.4 | 95.9–180.0 |
| HD657 | " | 154.4 | 103.4–223.8 |
| HD 240 | galleriae | 2027.6 | 998.6–4530.6 |
| PG 14 | morrisoni | 117.9 | 88.3–156.9 |
| HD 753 | darmstadiensis | 144.0 | 84.9–216.5 |
| HD 754 | " | 330.2 | 225.6–537.5 |
| HD 573 | wuhanensis | 2304.9 | 1575.4–3064.0 |
| HD 541 | kyushuensis | 31.4 | 20.9–42.3 |
| HD 571 | " | 12.5 | 9.2–16.9 |

Thirteen isolates involving 11 other sub-species had little or no activity (0 to 77% mortality at the very high dose of 10,000 ug of *B. thuringiensis* powder/g medium).

TABLE 2

The effect of two strains of *Bacillus thuringiensis* and diflubenzuron on the total number of *Lycoriella auripila* flies emerging from treated casing.

(a) Strain HD541

| Treatment | HD541 | | | | Dif* | Control |
|---|---|---|---|---|---|---|
| Rate ~ | 0.4 | 2.0 | 10.0 | 50.0 | 30.0 | — |
| Total No | 1602 | 1301 | 901 | 192 | 193 | 2071 |
| % of Control | 77.4 | 62.8 | 43.5 | 9.3 | 9.3 | 100.0 |

(b) Strain HD571

| Treatment | HD571 | | | | Dif* | Control |
|---|---|---|---|---|---|---|
| Rate ~ | 4.0 | 10.0 | 25.0 | 62.5 | 30.0 | — |
| Total No | 313 | 81 | 31 | 10 | 22 | 754 |
| % of Control | 41.5 | 10.7 | 4.1 | 1.3 | 2.9 | 100.0 |

*Diflubenzuron formulated as a 25% wettable powder
~HD 571 & HD 541, mls broth/kg casing; Diflubenzuron, mg a.i./kg

TABLE 3

Activity of B. thuringiensis HD571 formulations against Lycoriella auripila

| Formulation | Activity[1] |
| --- | --- |
| Culture broth | 100 |
| Spray-dried culture broth | 85 |
| WP 50[2] | 80 |
| SC 100[3] | 85 |
| SC 200[4] | 65 |

[1] Activity expressed as % of control achieved by diflubenzuron. Formulations were added to casing at 0.625 g per kg (or equivalent).
[2] Wettable powder containing 50% B. thuringiensis HD571 and prepared as described in Example 4.
[3] Suspension concentrate (diluted 10 fold) prepared as described in Example 4.
[4] Suspension concentrate (diluted 5 fold) prepared as described in Example 4.

We claim:

1. A method for the biological control of Dipteran pests of the genus Lycoriella, comprising contacting the pests with a Lycoriella controlling effective amount of a strain of *Bacillus thuringiensis* sub-species *kyushuensis* selected from group consisting of *Bacillus thuringiensis* HD541 (NCIMB 40373), *Bacillus thuringiensis* HD571 (NCIMB 40374) and mutants thereof having the same insecticidal activity.

2. The method according to claim 1 which the Dipteran pests of the genus Lycoriella are those which affect plants and edible fungi.

3. The method according to claim 1 wherein the Dipteran pests of the genus Lycoriella are mushroom pests.

4. The method according to claim 1 wherein the Dipteran pests of the genus Lycoriella are *Lycoriella auripila* or *Lycoriella mali*.

* * * * *